United States Patent [19]
Schmolka

[11] 4,360,451
[45] Nov. 23, 1982

[54] AMPHOTERIC SURFACTANT GELS

[75] Inventor: Irving R. Schmolka, Grosse Ile, Mich.

[73] Assignee: BASF Wyandotte Corporation, Wyandotte, Mich.

[21] Appl. No.: 291,337

[22] Filed: Aug. 10, 1981

[51] Int. Cl.$^3$ .............................................. B01J 13/00
[52] U.S. Cl. .................................... 252/316; 424/70; 424/78; 525/409
[58] Field of Search .................... 252/316; 424/70, 78; 525/409

[56] References Cited

U.S. PATENT DOCUMENTS

| | | | |
|---|---|---|---|
| 3,579,465 | 5/1971 | Schmolka | 252/316 |
| 3,740,421 | 6/1973 | Schmolka | 424/70 X |
| 3,748,276 | 7/1973 | Schmolka | 252/316 |
| 3,925,241 | 12/1975 | Schmolka | 252/316 |
| 4,061,602 | 12/1977 | Oberstar et al. | 424/70 X |

*Primary Examiner*—Lucille M. Phynes
*Attorney, Agent, or Firm*—Joseph D. Michaels

[57] ABSTRACT

Amphoteric surfactant gels containing a polyoxybutylene-polyoxyethylene block copolymer which maintain their gel characteristics at temperatures below about 20° C.

6 Claims, No Drawings

AMPHOTERIC SURFACTANT GELS

BACKGROUND OF THE INVENTION

1. Field of the Invention

The invention relates to an amphoteric surfactant gel comprising (a) from about 5 parts by weight to about 50 parts by weight amphoteric surfactant (b) from about 10 parts by weight to about 80 parts by weight of water and from about 15 parts by weight to about 40 parts by weight of a polyoxybutylene-polyoxyethylene block copolymer. These gels may be used for shampoos, hand and facial cleansers, eye makeup, removers, surgical scrubs, and bath or shower gels. All these gels are distinguished by the fact that they are liquid at elevated temperature but are gels below about 20° C.

2. Description of the Prior Art

U.S. Pat. No. 3,925,241 relates to amphoteric surfactant gels containing certain polyoxypropylene-polyoxyethylene block copolymers as gelling agents. These gels may be made by adding an amphoteric surfactant to a solution of water and block copolymer at a temperature of 7° C. to 10° C. while mixing. The solution is then allowed to warm to room temperature resulting in a ringing gel.

Among the problems of the prior art gels are their inability to be used in cold climates since they lose their gel characteristics below about 10° C. It has now been discovered that it is possible to prepare gels incorporating amphoteric surfactants devoid of the above problems.

SUMMARY OF THE INVENTION

The invention relates to an amphoteric surfactant gel comprising, based on a total of 100 parts by weight, (a) from about 5 parts by weight to about 50 parts by weight of an amphoteric surfactant, (b) from about 10 parts by weight to about 80 parts by weight of water, and (c) from about 15 parts by weight to about 40 parts by weight of a polyoxybutyelne-polyoxyethylene block copolymer, said block copolymer being a cogeneric mixture of conjugated polyoxy-butylene-polyoxyethylene compounds containing in their structure oxybutylene groups, oxyethylene groups and an organic radical derived from an organic compound containing a plurality of reactive hydrogen atoms, preferably a water soluble organic compound containing a plurality of reactive hydrogen atoms and 2 to 12 carbon atoms. The compounds are characterized in that all the oxybutylene groups are present in polyoxybutylene chains that are attached to the organic radical at the site of a reactive hydrogen atom thereby principally constituting a polyoxybutylene polymer. The oxyethylene groups are attached to the polyoxybutylene polymer in polyoxyethylene chains. The average molecular weight of the polyoxybutylene polymers in the mixture is at least 1200, as determined by hydroxyl number and the oxyethylene groups present constitute about 50 to about 80 percent by weight of the compound, with the provisos that (a) when the hydrophobe molecular weight is about 1200, then the minimum polyoxyethylene content is about 60 percent by weight of the block copolymer and the minimum block copolymer content to form a gel is about 25 percent by weight of the aqueous gel compositions; (b) when the hydrophobe molecular weight is about 1800, then the minimum polyoxyethylene content is about 55 percent by weight of the block copolymer and the minimum block copolymer content to form a gel is about 20 percent by weight of the aqueous gel composition; (c) when the hydrophobe molecular weight is about 2400, then the minimum polyoxyethylene content is about 50 percent by weight of the block copolymer and the minimum block copolymer content to form a gel is about 16 percent by weight of the aqueous gel composition; (d) when the hydrophobe molecular weight is about 3000, then the minimum polyoxyethylene content is about 45 percent by weight of the block copolymer and the minimum block copolymer content to form a gel is about 16 percent by weight of the aqueous gel composition. The amphoteric surfactant gels are useful as hair shampoos, hand and facial cleansers, particularly at temperatures below 20° C.

DESCRIPTION OF THE PREFERRED EMBODIMENTS

The block copolymer of use in the invention is a cogeneric mixture of conjugated polyoxybutylene polyoxyethylene compounds having as a hydrophobe, a polyoxybutylene polymer of at least 1200 molecular weight. The polyoxybutylene compounds are prepared by first condensing butylene oxide with an organic compound containing a plurality of reactive hydrogen atoms to prepare a polyoxybutylene polymer of at least 1200 molecular weight, and subsequently condensing ethylene oxide thereto. The compounds used in this invention conform to the following generic formula.

$$Y[(C_4H_8O)_n\text{-}E\text{-}H]_x \qquad (A)$$

wherein Y is the residue of a water soluble organic compound containing therein x active hydrogen atoms; n is an integer; x is an integer greater than 1; the values of n and x are such that the molecular weight of the compound, exclusive of E, is at least 1200 as determined by hydroxyl number, E is a polyoxyalkylene chain wherein the oxygen/carbon atom ratio is at least 0.5, and E constitutes 50 percent by weight to 80 percent by weight of the compound.

The polyoxybutylene polymer, which is an intermediate in the preparation of the compounds of use in this invention, has the following structure:

$$Y[(C_4H_8O)_nH]_x \qquad (B)$$

wherein Y, n and x are defined as in Formula A above.

The preferred compounds of use in this invention are prepared by condensing ethylene oxide in an amount between 50 and 80 percent by weight of the resultant compound, with the polyoxybutylene polymer. These compounds have the following formula $$Y[(C_4H_8O)_n(C_2H_4O)_mH]_x \qquad (C)$$

wherein Y, n and x are defined as in Formula A and m has a value such that the oxyethylene groups constitute 50 to 80 percent by weight of the compound.

When ethylene oxide is condensed with a polyoxybutylene glycol of at least 1200 molecular weight and derived from a butane diol initiator, the resulting compounds have the following structure:

$$HO(C_2H_4O)_{m'}(C_4H_8O)_n(C_2H_4O)_{m}H \qquad (D)$$

where n is defined as previously set forth, and $m'+m$ have a value such that the oxyethylene groups constitute 50 percent by weight to 80 percent by weight of the compound.

The hydrophilic portion of the polyoxyalkylene compounds may be supplied in whole or in part by other polyoxyalkylene chains in lieu of the polyoxyethylene chain set forth in Formula C. Any polyoxyalkylene chain may be used provided that the oxygen/carbon ration contained therein is at least 0.5.

Examples of a water-soluble organic compound containing therein x active hydrogen atoms, the residue of which is Y, are the initiators, which may include water, diols such as propane diol, butane diol, triols such as glycerol, tetrols such as pentaerythritol as well as initiators containing more than four hydroxyl groups such as hexitol or sucrose. Also, amines and other low molecular weight water-soluble compounds having two or more active hydrogen atoms such as ethylene diamine or diethylene triamine may be used as the initiator. Preferably used is butane diol. More preferably used is 1,4-butanediol.

The butylene oxide used in making the hydrophobic polyoxybutylene polymer, which is an intermediate in the preparation of the compounds used in this invention, may be replaced with up to 10 percent by weight of propylene oxide or ethylene oxide when added as a mixture with the butylene oxide. Also, up to 10 percent by weight of propylene oxide or butylene oxide may be used to replace ethylene oxide, when added as a mixture with ethylene oxide, in preparing the block copolymers used in this invention. In lieu of butylene oxide, other 4-carbon cyclic ethers such as methyloxetane, tetrahydrofuran and isobutylene oxide may be used.

Useful block copolymers, conforming to structure D above, of use in this invention, are those block copolymers which contain a hydrophobe of about 1800 average molecular weight and an ethylene oxide content of about 65 percent, forming a gel at a minimum of 25 percent by weight block copolymer in water; a hydrophobe of about 1800 average molecular weight and an ethylene oxide content of about 60 percent, forming a strong ringing gel at a minimum of 30 percent by weight block copolymer in water; and other gels formed from block copolymers with hydrophobe average molecular weights of 1200, 1400, 2000, 2200, and higher, an ethylene oxide content of about 50 percent by weight to about 80 percent by weight of the block copolymer; and which form a gel from a minimum of about 16 percent by weight block copolymer concentration in water. Preferably used is a block copolymer conforming to structure D above of use in the invention containing a hydrophobe of about 1800 average molecular weight, about 70 percent by weight relative to the weight of block copolymer of ethylene oxide and giving a block copolymer of about 6000 molecular weight. This block copolymer forms a gel at about 20 percent by weight in water. These block copolymers are used in an amount of between about 15 percent by weight to about 40 percent by weight, preferably about 18 percent by weight to about 25 percent by weight, based on the weight of amphoteric surfactant gel.

The amphoteric surfactants which are employed in the present invention are surface-active agents containing both basic and acidic groups in the same molecule. These groups may be anionic or cationic and the molecule may contain several such groups. Examples of these amphoteric surfactants include the alkyl-substituted imidazolines such as: 2-alkyl-1-carboxymethyl-1-hydroxyethyl-2-imidazolinium hydroxide and 2-alkyl-1-carboxymethyl-1-carboxymethyl hydroxyethyl-1-alkyl sulfate imidazoline wherein the alkyl group may be derived from coconut, lauric, capric, caprylic, ethylhexoic, oleic, linoleic, or stearic acid alkyl 3-aminopropionic acids wherein the alkyl group may be coconut, tallow or lauryl; the alkyl betaines wherein the alkyl groups may be coconut, tallow, stearyl or lauryl; fatty acid amide sulfonates wherein the fatty acid groups may be stearic, lauric, capric, oleic, caprylic, or linoleic; the alkyl $\beta$-aminopropionic acids wherein the alkyl grouping may be lauryl, myristyl, coconut, or stearyl; the amphoteric derivatives of polypeptides; and alkyl(ethyl-$\beta$-oxypropanoic)imidazoline wherein the alkyl group may contain from 7 to 17 carbon atoms. Other suitable amphoteric surfactants, useful in the gels of the invention, are disclosed in U.S. Pat. Nos. 3,849,548, 3,959,462 and 4,061,602. The amphoteric surfactants are used in an amount between 5 and 50, preferably 20 and 40, percent by weight of the amphoteric surfactant gel.

For the preparation of gels, incorporating amphoteric surfactants, of improved stability, the polyoxybutylene-polyoxyethylene block copolymers are heated to a temperature of at least 50° C. or higher. The procedure is as follows: water, the amphoteric and the block copolymer are placed in a vessel, heating to about 60° C. with gentle mixing until a clear homogeneous solution is obtained. The solution is then allowed to cool to a temperature of about 35° C., resulting in a ringing gel.

Any of the conventional additives such as dyes, perfumes, and preservatives may also be added to the solution after adding the amphoteric surfactant and before allowing the solution to cool to a temperature below about 35° C.

As used herein, the term "gel" is defined as a solid or semisolid colloid containing considerable quantities of water. The particles in a gel are linked in a coherent meshwork which immobilizes the water. The colloidal solution with water as a dispersion medium is often called a "hydrosol". The gels within the scope of the present invention are more specifically "ringing" gels and may be described as gels that have a firm, jelly-like consistency; that is, by tapping the gel lightly, it will vibrate and return to its original configuration.

Not all of the block copolymers of formula D above may be employed in the present invention. Because of the nature of aqueous solutions of these block copolymers, three variables affect the formation of the gels. These variables are: the weight percent concentration of block copolymers in the gel, the molecular weight of the hydrophobe $(C_4H_8O)_n$ and the percent by weight of the hydrophile portion $(C_2H_4O)_m + (C_2H_4O)_{m'}$ of the copolymer. These minima define a minimum weight percent concentration of the block copolymer with a specific molecular weight polyoxybutylene hydrophobe having a minimum weight percent of ethylene oxide condensed thereto that is necessary to form a gel. Thus, at the minimum concentration with a specific molecular weight hydrophobe, a minimum weight percent of ethylene oxide is required before a specific block copolymer will form a gel in an aqueous solution.

Illustrative block copolymers of formula D above which may be employed in the preparation of the gels of the present invention made from a polyoxybutylene hydrophobe prepared from condensing 1,2-butylene oxide with a 1,4-butanediol initiator, are presented in Table I.

The minimum weight percent concentrations with specific molecular weight hydrophobes are set out in Table II.

TABLE I

| Block Copolymer | Molecular Weight of Hydrophobe (Avg.) | Weight Percent of Hydrophile (Avg.) | Approximate Total Molecular Weight of Copolymer | |
|---|---|---|---|---|
| | | | T | F |
| A | 1800 | 60 | 4500 | 4200 |
| B | 1800 | 70 | 6000 | 5700 |
| C | 1800 | 80 | 9000 | 8130 |
| D | 1200 | 70 | 4000 | 3765 |
| E | 1200 | 80 | 6000 | 5160 |
| F | 2400 | 60 | 6000 | 5670 |
| G | 2400 | 70 | 8000 | 7800 |
| H | 2400 | 80 | 12,000 | 11,000 |
| I | 3000 | 60 | 7500 | 6165 |
| J | 3000 | 70 | 10,000 | 9000 |
| K | 3000 | 80 | 15,000 | 11,000 |
| L | 1200 | 60 | 3,000 | 2,922 |

TABLE II

| Molecular Weight of Hydrophobe | Minimum Percent by Weight of Block Copolymer to form Aqueous Gel | Minimum Percent by Weight of Ethylene Oxide Required |
|---|---|---|
| 1200 | 25 | 60 |
| 1800 | 20 | 55 |
| 2400 | 16 | 50 |
| 3000 | 16 | 45 |

The gels of the present invention comprise, based on a total of 100 parts by weight, (a) from about 15 parts to 40 parts, preferably from about 18 parts to 25 parts, of polyoxybutylene-polyoxyethylene block copolymer; (b) from about 10 parts to about 80 parts, preferably from about 30 parts to about 60 parts, more preferably from 40 parts to 50 parts, of water; and (c) from 5 parts to 50 parts, preferably from 20 parts to 40 parts of amphoteric surfactant.

The technical explanation for the formation of the gels of the invention is not entirely understood, and the explanation hereinafter is not to be considered as being limitative of the invention. However, the behavior of these block copolymers in forming the gels is believed to be explained on the basis of hydrate formation. It may be speculated that the hydrophobe may, in its own right, immobilize the water independently of the oxyethylene chain by hydrogen bonding. It should be noted that the preferred block copolymers used in the gels of this invention exhibit a hydrophobe lying between two equal hydrophiles. This structure suggests a loose micellar structure is obtained with this class of nonionics and that gel formation would readily involve entrapment of free water in addition to water due to hydrogen bonding.

The following examples will further illustrate the various aspects of the invention. Where not otherwise specified throughout the specification and claims, temperatures are in degrees centigrade, parts, percentages and proportions are by weight.

The following amphoteric Surfactants P-R are used in the examples: Amphoteric P is MIRANOL 2 MCAS modified. Amphoteric Q is MIRANOL BT. Amphoteric R is MIRANOL MHT. Each of the above amphoterics is a long chain imidazoline type of zwitterion.

EXAMPLE 1

An amphoteric surfactant gel was prepared for use as a hand or facial cleanser by placing the following components in a vessel, heating to about 140° F. and mixing until a clear solution is obtained. The solution was then allowed to cool to room temperature, about 20° C., resulting in a ringing gel.

| Component | Parts by Weight |
|---|---|
| Block Copolymer B | 24 |
| Amphoteric P | 30 |
| Water | 46 |

EXAMPLE 2

Example 2 was prepared using the general procedure of Example 1 to give an amphoteric surfactant gel of the following composition components:

| Component | Parts by Weight |
|---|---|
| Block Copolymer B | 23 |
| Amphoteric Q | 35 |
| Water | 42 |

EXAMPLE 3

Example 3 was prepared following the procedure of Example 1 to give an amphoteric surfactant gel having the following composition:

| Component | Parts by Weight |
|---|---|
| Block Copolymer B | 35 |
| Amphoteric Q | 35 |
| Water | 40 |

EXAMPLE 4

The procedure of Example 1 was followed to prepare an amphoteric surfactant gel having the following composition:

| Component | Parts by Weight |
|---|---|
| Block Copolymer B | 25 |
| Amphoteric R | 35 |
| Water | 40 |

EXAMPLE 5

The procedure of Example 1 is followed to prepare an amphoteric surfactant gel having the following composition:

| Component | Parts by Weight |
|---|---|
| Block Copolymer G | 25 |
| Amphoteric P | 40 |
| Water | 35 |
| Bactericide, Perfume | q.s. |

The amphoteric surfactant gels of the invention described above do not liquify when cooled to below room temperature, i.e., about 20° C. or colder.

The embodiments of the invention in which an exclusive privilege or property is claimed are defined as follows:

1. An amphoteric surfactant gel comprising based on the total of 100 parts by weight (a) from about 5 to about 50 parts by weight of amphoteric surfactant, (b) from about 10 to about 80 parts by weight of water, (c) from about 15 to about 40 parts by weight of a polyoxybutylene-polyoxyethylene block copolymer, said block copolymer being a cogeneric mixture of conjugated polyoxybutylene-polyoxyethylene compounds containing in their structure oxybutylene groups, oxyethylene groups and an organic radical derived from a water-soluble organic compound containing a plurality of reactive hydrogen atoms and 2 to 12 carbon atoms; the compounds being characterized in that all of the oxybutylene groups are present in polyoxybutylene chains that are attached to the organic radical at the site of a reactive hydrogen atom thereby constituting a polyoxybutylene polymer; the oxyethylene groups being attached to the polyoxybutylene polymer in polyoxyethylene chains; the average molecular weight of the polyoxybutylene polymers in the mixture being at least 1200, as determined by hydroxyl number, and the oxyethylene groups present constituting 50 to 80 percent, by weight, of the mixture, with the provisos that (a) when the hydrophobe molecular weight is about 1200, then the minimum polyoxyethylene content is about 60 percent by weight of the block copolymer and the minimum block copolymer content to form a gel is about 25 percent by weight of the aqueous gel compositions;

(b) when the hydrophobe molecular weight is about 1800, then the minimum polyoxyethylene content is about 55 percent by weight of the block copolymer and the minimum block copolymer content to form a gel is about 20 percent by weight of the aqueous gel composition;

(c) when the hydrophobe molecular weight is about 2400, then the minimum polyoxyethylene content is about 50 percent by weight of the block copolymer and the minimum block copolymer content to form a gel is about 16 percent by weight of the aqueous gel composition;

(d) when the hydrophobe molecular weight is about 3000, then the minimum polyoxyethylene content is about 45 percent by weight of the block copolymer and the minimum block copolymer content to form a gel is about 16 percent by weight of the aqueous gel composition.

2. The amphoteric surfactant gel of claim 1 wherein the block copolymer comprises from about 18 to about 25 parts by weight of the amphoteric surfactant gel.

3. The amphoteric surfactant gel of claim 1 wherein the polyoxybutylene polymer has an average molecular weight of about 1800 and a polyoxyethylene content of about 70 percent by weight of the mixture.

4. The amphoteric surfactant gel of claim 2 wherein the polyoxybutylene polymer has an average molecular weight of about 1800 and a polyoxyethylene content of about 70 percent by weight of the mixture.

5. The amphoteric surfactant gel of claim 1 wherein the amphoteric surfactant comprises from about 20 to about 40 parts by weight of the amphoteric surfactant gel.

6. The amphoteric surfactant gel of claim 1 wherein the water comprises from about 30 to about 60 parts by weight of the amphoteric surfactant gel.

* * * * *